United States Patent [19]

Coval

[11] 4,165,370
[45] Aug. 21, 1979

[54] INJECTABLE GAMMA GLOBULIN

[76] Inventor: Myer Louis Coval, 6241 Chelton Dr., Oakland, Calif. 94611

[21] Appl. No.: 900,616

[22] Filed: Apr. 27, 1978

Related U.S. Application Data

[60] Division of Ser. No. 688,621, May 21, 1976, Pat. No. 4,093,606, which is a continuation-in-part of Ser. No. 550,467, Feb. 18, 1975, abandoned.

[51] Int. Cl.² .................... A61K 39/00; A61K 39/42; A61K 37/00; C07G 7/00
[52] U.S. Cl. .................... 424/85; 260/112 B; 424/177; 424/86; 424/87
[58] Field of Search .................... 260/112 B; 424/177, 424/86, 87, 85

[56] References Cited

U.S. PATENT DOCUMENTS

| | | | |
|---|---|---|---|
| 2,437,060 | 3/1948 | Williams et al. | 260/112 B |
| 2,793,203 | 5/1957 | Schultze et al. | 260/112 B |
| 2,867,567 | 1/1959 | Bidwell | 260/112 B |
| 3,763,135 | 10/1973 | Shanbrom et al. | 260/112 B |
| 3,808,189 | 4/1974 | Breuer | 260/112 B |
| 3,869,436 | 3/1975 | Falksveden et al. | 260/112 B |
| 3,880,989 | 4/1975 | Garcia et al. | 260/112 B |
| 3,916,026 | 10/1975 | Stephan | 424/177 |
| 3,943,245 | 3/1976 | Silverstein | 260/112 B |
| 3,984,539 | 10/1976 | Khouw et al. | 260/112 B |
| 4,000,121 | 12/1976 | Garcia | 260/112 B |
| 4,018,885 | 4/1977 | Bohn et al. | 424/177 |
| 4,021,540 | 5/1977 | Pollack et al. | 260/112 R |
| 4,025,500 | 5/1977 | Garcia et al. | 424/177 |

FOREIGN PATENT DOCUMENTS 1198277  10/1967  United Kingdom .................. 260/112 B

OTHER PUBLICATIONS

W. Stephen, Chem. Abst., 71, 1969, p. 47731v.
W. Stephen, Chem. Abst., 75, 1971, p. 17954k.
E. W. Martin et al., "Practice of Pharmacy", 1961, pp. 218 & 219.
B. Holpern et al., Chem. Abst., 71, 1969, p. 116535y.
Chem. Abst., 72, 1970, p. 136440n.

*Primary Examiner*—Delbert R. Phillips
*Attorney, Agent, or Firm*—Robert G. Slick

[57] ABSTRACT

A process is provided for the preparation of a gamma globulin suitable for intravenous administration from the readily available Fraction II or II + III plasma protein paste. The Fraction II or II + III paste is extracted with water at a pH of 4.8–6.5 and impurities are fractionally precipitated by addition of polyethylene glycol to 4% of wt./vol. and then 5% wt./vol. The desired gamma globulin is then precipitated at a pH 8.0 by addition of polyethylene glycol to 12% wt./vol.

3 Claims, 1 Drawing Figure

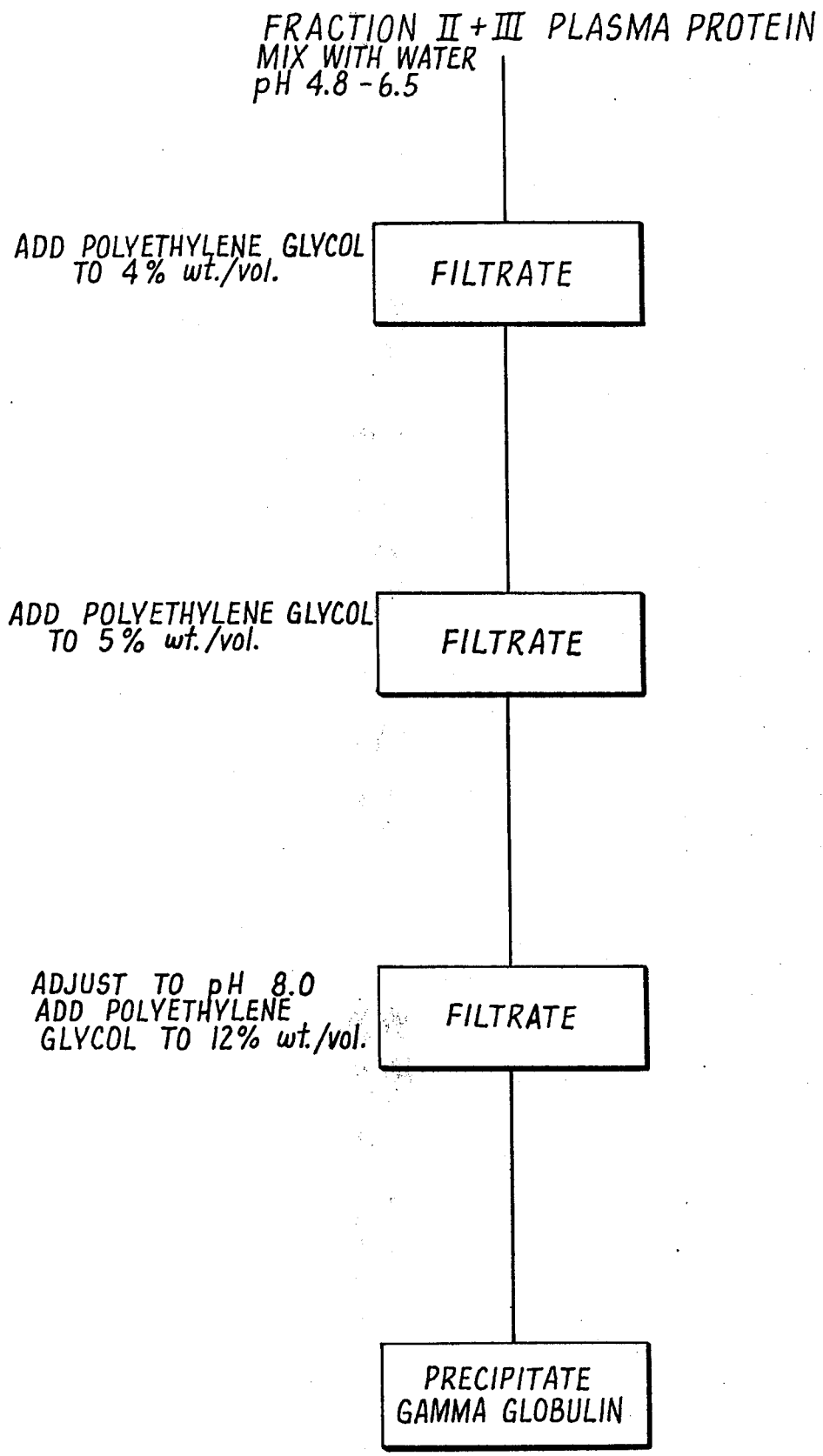

INJECTABLE GAMMA GLOBULIN

REFERENCE TO RELATED APPLICATION

This is a division of application Ser. No. 688,621, filed May 21, 1976, now U.S. Pat. No. 4,093,606. which in turn is a continuation-in-part of my application Ser. No. 550,467 filed Feb. 18, 1975 now abandoned.

SUMMARY OF THE INVENTION

This invention relates to gamma globulins. It particularly relates to a gamma globulin preparation suitable for administration by intravenous injection and to processes for the preparation of said gamma globulin.

The gamma globulin, Immunoglobulin G (IgG) fraction of pooled plasma contains antibodies to many infectious agents. Immunoglobulins are effective in the clinical management of a wide variety of disease states. They are used in prophylaxis and therapy of infections in patients with various antibody deficiency states. In patients with normal immunoglobulin levels, they are used in prophylaxis of viral infections, such as, for example, hepatitis, measles, German measles, chicken pox, mumps, yellow fever, rabies, herpes and smallpox; bacterial infections such as, for example, diphtheria, pertussis and tetanus, Rh-incompatibility, and in the therapy of severe antibiotic-resistant bacterial infections (Staphylococcus and *Coli sepsis,* Pseudomonas and *Pyocyaneaus septicemia*). The full clinical potential of immunoglobulins has not yet been determined.

Human immunoglobulins were first isolated on a large scale during World War II. It was soon observed that intravenous injection of these preparations caused shock reactions in some patients, and it was subsequently established that the anticomplementary activity of IgG preparations is responsible for the shock reactions. This anticomplementary activity is due to IgG aggregates formed during the fractionation.

In view of these shock reactions associated with the intravenous administration of the immunoglobulins, these therapeutically useful substances were administered intramuscularly instead. However, the intramuscular administration of immunoglobulins has many limitations:

a. they are painful;
b. the amount which can be administered is limited;
c. proteolysis at the site of injection decreases the available IgG;
d. maximum blood levels are attained only after three to four days, which is a serious handicap in those cases requiring high blood levels of IgG immediately after injection.

Furthermore, intravenous administration of immunoglobulins has wider clinical application because the full dose of IgG enters the blood stream immediately without being degraded at the site of injection, and significantly higher blood levels can be attained. These considerations have prompted the search for methods to prepare IgG with low anticomplementary activity which is suitable for intravenous use. The methods which have been developed are based on proteolytic or chemical treatment to abolish the anticomplementary properties of the aggregates.

Examples of preparations obtained by these methods are:

(1) Pepsin-treated Immunoglobulin. In this preparation the protein is extensively degraded to antibody fragments (5S, F(ab')2). Its usefulness for combating bacterial infections is limited because it has a short-life (about 30 hours compared with 20 to 30 days for native IgG). After combining with anti-gens, the 5S fragments do not fix complement. It has no application in prophylaxis. (2) Plasmin-treated Immunoglobulin. More than 60 percent of this preparation is degraded to fragments (Fab and Fc). The remaining 7S globulin has a normal half-life (three to four weeks), but the antibody spectrum is limited. (3) pH 4-treated Immunoglobulin. This preparation has a tendency to become anticomplementary during storage. Its compatibility is therefore restricted and high doses cannot be administered. The half-life is slightly reduced (12 to 14 days) and the antibacterial activity is reduced to an unknown degree. (4) B-Propiolactone-Treated Immunoglobulin. The molecules are extensively altered, probably forming new antigenic determinants. The half-life is about 10 days. The bacteriolytic activity is reduced.

The four IgG subclasses have different susceptibilities to proteolysis. The pepsin, plasmin and pH 4 (pepsin) preparations accordingly differ markedly from untreated IgG in their subclass distribution.

As noted above, the undesirable anticomplementary activity which is responsible for the shock reaction produced by the intravenous administration of IgG is due to the aggregates present therein, which aggregates are formed during the fractionation procedures used in the preparation. The preparations described above are obtained by methods which use procedures to destroy these aggregates after they formed, in most cases by either chemical or enzymatic degradation. However, such degradation procedures also result in some degradation of the IgG with consequent loss of activity, so such preparations as described above are not as active as desired. Little work has been done on developing methods which prevent the formation of aggregates and provide IgG preparations having substantially no anticomplementary activity.

More recently, there has been disclosed in German Offenlegungsschrift No. 2,357,800, published June 6, 1974, a method for the preparation of a gamma globulin suitable for intravenous administration. This procedure, as well as other published procedures for the preparation of gamma globulin, requires as starting material a relatively purified gamma globulin fraction. However, of greater significance, the gamma globulin obtained by this method still possesses an excessively high anticomplementary activity for intravenous use.

It has also been proposed (U.S. Pat. No. 3,763,135) to prepare a material suitable for intravenous injection from Fraction III but the process of the present invention gives a much larger yield and the product is much lower in anticomplementary material.

There are Food and Drug Administration standards for intramuscular gamma globulin, but not for intravenous gamma globulin. Such standards are needed to distinguish between gamma globulin which causes shock-like reactions when given by the intravenous route to sensitive individuals and gamma globulin which does not elicit such reactions.

During the past fifteen years, it has been established that no clinical symptoms are observed, even in highly sensitive recipients, when the level of anticomplementary activity is sufficiently low. With the unit of the standard Mayer two unit assay (EXPERIMENTAL IMMUNOCHEMISTRY, by E. A. Kabat and M. M. Mayer 2nd Ed., p. 133, Thomas, Springfield, Ill., 1961), the safe level is 0.04 to 0.02 units or less of anticomplementary material per milligram of Immunoglobulin G, and may be somewhat higher than 0.04, but reactions are routinely observed when the level is 0.4 per milligram. The designation of gamma globulin preparations as suitable for intravenous use, signifying the absence of clinical reactions, is dependent on a specific low level of anticomplementary activity. It is also necessary to preserve the physiological antibody activity and specificity, in order to provide a clinically safe and effective preparation.

The methods of this patent application have been designed to produce a product which retains the properties of the native gamma globulin molecules, and is essentially devoid of aggregates and their anticomplementary activity, thereby rendering the product safe and effective for intravenous use.

It is, accordingly, an object of the present invention to provide a gamma globulin preparation suitable for intravenous injection.

It is another object of the present invention to provide a gamma globulin preparation suitable for intravenous injection, which has substantially no anticomplementary activity in vitro.

It is a further object of the present invention to provide a gamma globulin preparation suitable for intravenous injection, which has a biological half-life of about 3 to 4 weeks.

It is still another object of the present invention to provide a gamma globulin preparation suitable for intravenous injection, which has the ability to fix complement when combined with the corresponding antigen and which has an essentially unaltered antibody spectrum compared with the types and levels of gamma globulin antibodies present in the starting plasma pool and in standard gamma globulin obtained by Cohn's classical ethanol fractionation of plasma.

It is still a further object of the present invention to provide a method for preparing a gamma globulin preparation suitable for intravenous administration.

It is still another object of the present invention to provide a method for preparing from readily available blood protein fractions a gamma globulin preparation suitable for intravenous injection.

It is still a further object of the present invention to provide a method for preparing a gamma globulin preparation suitable for intravenous injection, in which method there is substantially no formation of aggregates.

The present invention provides an active gamma globulin suitable for intravenous administration, processes for the preparation of this gamma globulin, and stable, pharmaceutical preparations containing this gamma globulin.

In accordance with one aspect of the process of the present invention, the gamma globulin is obtained from the readily availble Fraction II+III of plasma proteins of Cohn et al as described in the J. Am. Chem. Soc. 68, 459–475 (1946). This fraction, which contains nearly all of the immunoglobulins in addition to other proteins is subjected to novel fractionation techniques which prevent the formation of the aggregates that formed during the fractionation procedures of the prior art and yield an active gamma globulin substantially devoid of anticomplementary activity and suitable for intravenous administration.

Another useful source of raw material is the Fraction II material which is readily available as immune serum globulin. This material is economical, stable as a freeze dried powder and is free of hepatitis virus. It can be processed in the same way as the Fraction II+III material.

BRIEF DESCRIPTION OF THE DRAWING

The sole FIGURE of the drawing is a flow diagram illustrating the process of the present invention.

DESCRIPTION OF THE PREFERRED EMBODIMENTS

In this process a paste of the Fraction II or II+III plasma proteins is extracted with water at a pH of from about 4.8 to 6.5, preferably from about 5.5 to 5.9. Pyrogen free water in a volume of about 25 to 45 liters, preferably 30 liters per kilogram of the paste having a protein content of about 25 to 30% is used. Any non-toxic pharmaceutically acceptable organic or inorganic acid, such as acetic, lactic, hydrochloric, sulfuric and the like may be used to adjust the pH. The water-insoluble material is separated and the filtrate is then subjected to fractional preciptations with polyethylene glycol at successive wt./vol. concentrations of 4, 5 and 12%, the last at a pH of about 8.0. The first two fractional precipitations remove impurities and the final precipitation yields the desired gamma globulin of the present invention. The preferred polyethylene glycol has a molecular weight of about 4,000 to 6,000. Any non-toxic, pharmaceutically acceptable inorganic or organic base can be used to adjust the pH to about 8.0. The process may be carried out at a temperature of from about 0° 1 to 20° C., but lower temperatures in the range of about 0° to 5° are preferred.

The process is described in detail in Examples 1 and 2. These examples are given by way of illustration and are not to be considered as limiting.

EXAMPLE 1

One kilogram of a paste of Fraction II+III plasma protein, having a protein content of 25 to 30% is suspended in 30 liters of pyrogen-free distilled water and stirred until a smooth yellow suspension is obtained. The temperature is maintained at 5° C. The pH is lowered to 5.8 by adding 20 ml. of 10% acetic acid to each kilogram of Fraction II and III paste. After 15 minutes of further stirring, the sediment is allowed to settle for two to three hours. The clear supernatant is then clarified by filtration using a filter such as Number 9 pads.

Polyethylene glycol (PEG), average molecular weight 4,000 grams per mole, U.S.P. grade, is added as powder or flake to a concentration of four grams per hundred milliliters of filtrate. This is stirred until the PEG suspension is dissolved, and the resulting precipitate is allowed to settle for one to two hours. The supernatant is collected by filtration through a filter acid as Number 9 pads or Millipore filters.

PEG concentration is then increased to five percent, weight/volume. The PEG is dissolved by stirring, and the solution is allowed to stand for one or more hours, after which the supernatant is again filtered through Number 9 asbestos pads.

The PH is then adjusted to pH 8 by the addition of 6 percent trishydroxy ethyl amino methane (THAM). The gamma globulin is then precipitated by the addition of PEG to 12 percent. When the white precipitate has settled, it is collected by centrifugation.

The gamma globulin thus obtained is an immunologically active unmodified IgG which has a titer of from about zero to 0.02 units per mg. of anticomplementary activity as determined by the method of Mayer, et al, which is described in Kabat and Mayer, Experimental Immunochemistry, 2nd Ed., Thomas (Springfield, Ill.), page 905 ff., and may be incorporated directly into pharmaceutical preparations for intravenous administration. The zero anticomplementary activity is due to the absence of aggregates, the formation of which does not occur during the fractionation steps of the process of the present invention. The non-formation of aggregates is due primarily to the use of polyethylene glycol and a medium of low-ionic strength in the fractionation which serve to reduce considerably any denaturation of proteins. The low conductance ($300 \times 10^{-6}$ cm$^{-1}$ ohm$^{-1}$) of the medium is an indication of its low ionic strength.

In addition to having practically zero anticomplementary activity, the gamma globulin prepared as described in Example I has a sedimentation coefficient of 7S and contains no aggregates and degradation products such as $F(ab)_1$, $F(ab)_2$ and Fc. Its aqueous solutions are clear and colorless, not opalescent or turbid like aqueous solutions of gamma globulins obtained by other methods. Unlike gamma globulin obtained by digestive methods, the gamma globulin of this invention has an antibody spectrum which is unaltered from that of the starting plasma. The subclass distribution of the gamma globulin of this invention (i.e. the relative amounts of IgG, 1, 2, 3, 4) is unaltered from that of the starting plasma.

EXAMPLE II

Two grams of Fraction II material are suspended in one liter of water containing 4% PEG 4000 at 3° C. The material is gently dissolved and 0.05 molar acetic acid is added to a pH of 5.1. After sitting for several hours, the material is clarified by filtration and the supernatant liquid recovered. The PEG concentration is then increased to 5% weight/volume. The PEG is dissolved by stirring and the solution allowed to stand for one or more hours after which the supernatant liquid is again filtered. The pH is then adjusted to pH 8 by the addition of 6% THAM. The gamma globulin is then precipitated by the addition of PEG to 12%. The precipitate is allowed to settle and is collected by centrifugation. The gamma globulin thus obtained is tested for anticomplementary activity as described under Example I, and has a titer of 0.02 to 0.005 units per mg.

The gamma globulin of this invention may be readily incorporated into pharmaceutical preparations suitable for intravenous administration. In formulating such preparation, the gamma globulin is dissolved in an aqueous solution buffered between about 5.4 to 6.7 and containing glycine, albumin and a non-ionic surfactant. The pH of the preparation is then adjusted as desired to a pH between about 5.4 to 6.7 and the concentration of the gamma globulin in the preparation is adjusted to 5%. Suitable buffers include phosphate and sodium acetate-acetic acid systems.

To prevent or reduce any denaturation at a liquid-air or liquid solid interface of the product in solution, it is advantageous to add a surfactant to the pharmaceutical composition. Suitable surfactants are non-ionic surfactants such as the block copolymers of propylene and ethylene oxides such as Pluronic 68 (poloxamer 188) and partial esters of sorbitol and polyoxethylene oxide of long chain fatty acids such as the Tweens 20, 40, 60, 80 and 85 (polysorbates 20, 40, 60, 80 and 95), water-soluble substances described in the 1973 edition of the Cosmetic, Toiletry and Fragrance Association, Inc. CTFA Cosmetic Ingredient Dictionary, and fluorosurfactants such as Zonyl FSA, FSB, FSC and FSN. These nonionic surfactants stabilize proteins against surface denaturation and do not contain as part of their structure any chemical groups which may otherwise interact with or denature proteins.

Example III illustrates the preparation of a pharmaceutical composition containing the gamma globulin of the present invention for intravenous administration.

EXAMPLE III

The precipitate prepared in Example I is dissolved in a solution containing: albumin, 5 grams per liter; Tween 80, 0.1%; glycine 0.15 M; sodium acetate 0.025 M, and acetic acid 0.0125 M at 5° C., with a minimum of frothing. The resulting pH is 5.4 to 5.5. If desired, it is adjusted to pH 6.4 with the cautious addition of THAM, 0.05 M. The concentration of IgG is then measured and the solution is adjusted to contain 5 grams of IgG per 100 ml. of solution either by dilution or by the addition of more precipitate from Example I. Other Tweens or Fluronic 68 may be used in place of Tween 80.

For a liquid product, the solution is then sterile-filtered and bottled.

For a lyophilized product, the liquid product is filled into vials and freeze dried. Before use, it is dissolved in pyrogenfree sterile water.

The gamma globulin of the present invention when stored in the pharmaceutical compositions of the present invention has a longer half-life than the other gamma globulin preparations now on the market. The gamma globulin of the present invention has proven to be useful for intravenous administration in all instances and for all conditions where the intravenous administration is desired without any of the usual undesirable effects associated with the intravenous administration of gamma globulins.

I claim:

1. A gamma globulin suitable for intravenous administration prepared according to the following process:
    a process for preparing a gamma globulin substantially devoid of anticomplementary activity and suitable for intravenous administration, from a material selected from the Fraction II+III plasma protein paste having a protein content of about 25—30% and Fraction II paste which comprises the steps:

a. suspending said paste in water to form a solution of low ionic strength having a conductance of about $300 - 10^{-6}$cm$^{-1}$ohm$^{-1}$ at a pH of about 4.8 to 6.5 to produce a precipitate and a filtrate, b. fractionally precipitating impurities from said filtrate by adding polyethylene glycol to 4% weight/volume and then 5% weight/volume, c. precipitating the gamma globulin by adding polyethylene glycol to 12% weight/volume at a pH of about 8.0.

2. A solution of the gamma globulin according to claim 1 for intravenous administration comprising the gamma globulin in a aqueous solution containing albumin, a non-ionic surfactant, glycine and acetic acid-acetate buffer at pH 5.4–6.7.

3. A solution of gamma globulin according to claim 2 wherein the non-ionic surfactant is Tween 80 or Pluronic 68.

* * * * *